United States Patent [19]

Martensson

[11] 3,996,107
[45] Dec. 7, 1976

[54] ENZYMATIC PRODUCTION OF A STARCH CONVERSION PRODUCT HAVING A HIGH MALTOSE CONTENT

[75] Inventor: Kaj Bennedick Martensson, Lund, Sweden

[73] Assignee: AB Stadex, Malmo, Sweden

[22] Filed: Aug. 28, 1974

[21] Appl. No.: 501,397

[30] Foreign Application Priority Data

Aug. 28, 1973 Sweden ............................ 7311642

[52] U.S. Cl. .............................. 195/31 R; 195/63; 195/68; 195/DIG. 11
[51] Int. Cl.$^2$ ........................................ C12D 13/02
[58] Field of Search ............... 195/DIG. 11, 31 R, 7, 195/11, 63, 68, 115

[56] References Cited

UNITED STATES PATENTS

| | | | |
|---|---|---|---|
| 3,627,638 | 12/1971 | Barker et al. | 195/63 |
| 3,677,896 | 7/1972 | Kurimoto et al. | 195/31 R |
| 3,702,804 | 11/1972 | Barker et al. | 195/63 |
| 3,720,583 | 3/1973 | Fisher et al. | 195/115 |
| 3,809,613 | 5/1974 | Vieth et al. | 195/DIG. 11 |
| 3,838,006 | 9/1974 | Hijiya et al. | 195/31 R |
| 3,843,446 | 10/1974 | Vieth et al. | 195/68 |
| 3,847,743 | 11/1974 | Forgione et al. | 195/63 |
| 3,849,253 | 11/1974 | Harvey et al. | 195/DIG. 11 |

OTHER PUBLICATIONS

Barker et al, "Enzyme Reactors for Industry", Process Biochemistry, vol. 6, No. 10, 1971 pp. 11–13.
Martensson et al., "Covalent Coupling of Pullulannse to an Acrylic Copolymer Using a Water–soluble Carbodimide," *Chemical Abstracts*, vol. 77, No. 17, p. 160, abs. No. 110853c (1972).

*Primary Examiner*—A. Louis Monacell
*Assistant Examiner*—Thomas G. Wiseman
*Attorney, Agent, or Firm*—Ladas, Parry, Von Gehr, Goldsmith & Deschamps

[57] ABSTRACT

The invention provides a method of enzymatic manufacturing of a starch conversion product having a high maltose content, using as a starting material a solution of a substrate, the method comprising bringing the substrate solution into contact with a matrix to which have been coupled both an α-1,6-glucosidase and an α-1,4-glucosidase having β-amylase activity.

10 Claims, 1 Drawing Figure

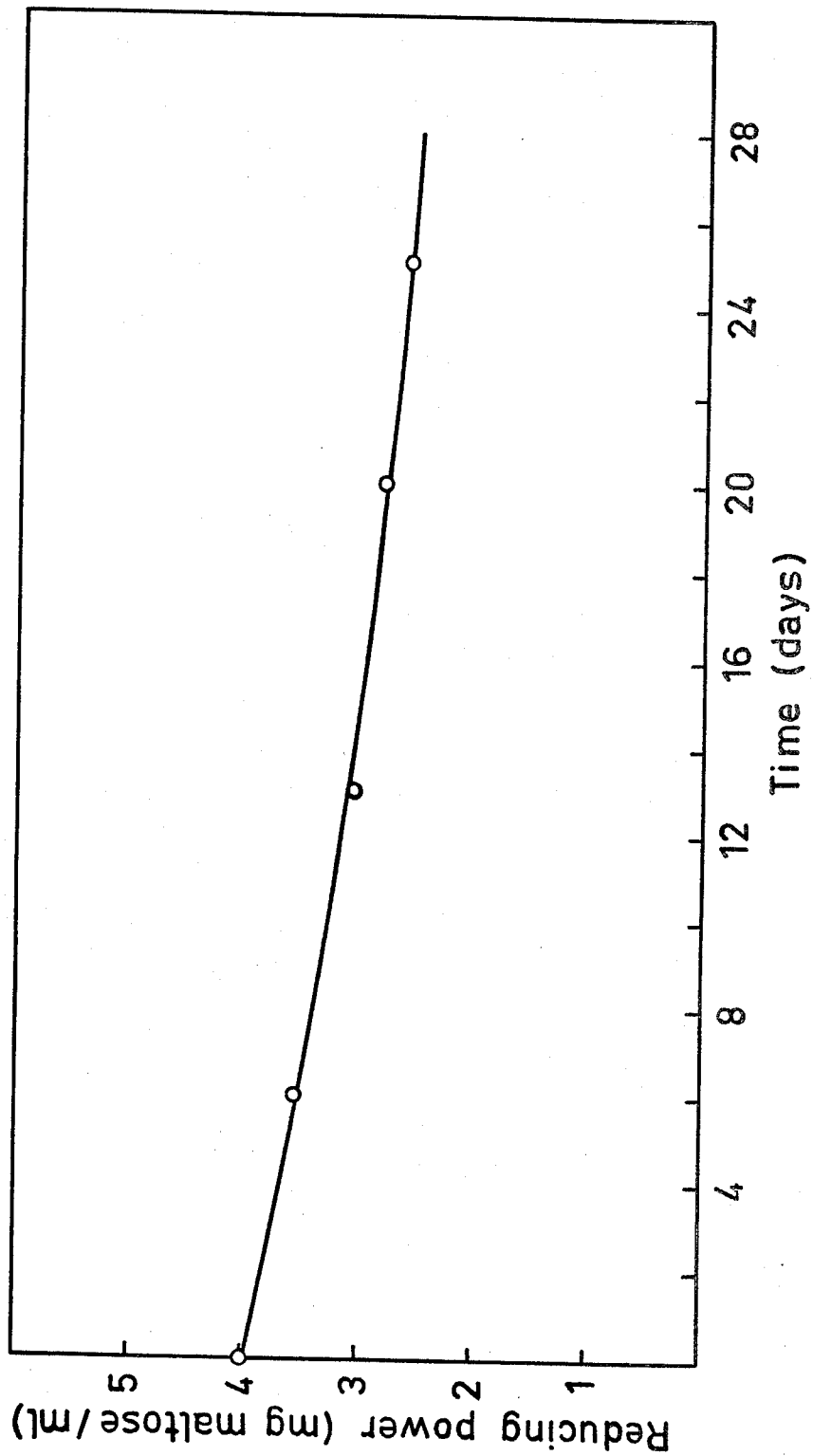

ENZYMATIC PRODUCTION OF A STARCH CONVERSION PRODUCT HAVING A HIGH MALTOSE CONTENT

The present invention relates to a method of enzymatic production of a starch conversion product having a high maltose content using a solution of a substrate comprising starch or a partial hydrolysate thereof as a starting material.

It is already known to produce maltose using a starch solution or a solution of a hydrolysate thereof by subjecting it to the influence of an α-1,4-glucosidase having β-amylase effect in combination with an α-1,6-glucosidase in such a way that the enzymes are used freely in the solution of starch or the hydrolysate thereof. This method has the drawback that the end product must in some way be purified from residual enzymes, another drawback of this prior art method being that the manufacturing of maltose must take place batchwise. The relatively expensive enzymes are further consumed in the process which entails unnecessarily high manufacturing costs.

The novel matter of the invention is to be seen in that the above substrate solution is brought into contact with a matrix to which both an α-1,6-glucosidase and an α-1,4-glucosidase having β-amylase activity have been coupled. By means of this coupling a so called two-enzyme system has been obtained. The use of this matrix bonded enzyme system implies that the cleansing step which was necessary in the prior art method can now be dispensed with. The use of the said matrix bonded system also implies that the manufacturing of a starch conversion product having a high maltose content can take place continuously for instance by bringing the substrate solution into contact with the matrix bonded system included in a suitable column. Thereby the process will also be very flexible with the possibilities of an automatic control of the composition of the end product by regulating the flow through the column (cf. table II). The above method will further permit recovering the enzymes throughout the process and consequently they can be reused as long as there is enough activity left. Coupling of various enzymes to matrices and their use in a series is previously known. It is a characteristic feature of the present invention that two different enzymes are coupled to the same matrix, said coupling being achievable by means of chemical and/or physical bonding, for instance adsorption, covalent bonding or steric inclusion in the structure of the matrix. By means of this method a substantial increase in stability is achieved for the two enzymes which permits longterm use in the process. Further, a very favourable system is achieved from a kinetic reaction point of view in which one enzyme facilitates the effect of the other by opening the steric configuration of the substrate. In this way the substrate need not be transported between the different matrix grains. The matrix material employed should be inert, i.e. resistant to enzymatic and microbial degradation under the conditions used in the method. Matrix materials to be employed for this purpose include cellulose derivatives, acrylic polymers, glass, dextran derivatives, agar derivatives, phenolic resins. Acrylic polymers have been found to be very suitable for matrix material.

In the method of the invention the starting material is a solution of a substrate comprising starch or a partial hydrolysate thereof and it is preferably to use as a starting material a starch hydrolysate having a dextrose equivalent of between 0.5 and 20, preferably between 5 and 10. To perform the method according to the invention a solution of starch hydrolysate in a concentration of between 10 and 40%, preferably between 30 and 35%, having a pH between 4.5 and 8.0, preferably between 5.5 and 6.5, and at a temperature of between 30° and 60° C, preferably between 40° and 50° C, is passed through a column containing the matrix bonded two-enzyme system. An example of the production of the matrix bonded enzyme system according to the invention will be given in example 1 below and the production of maltose according to the invention when the said enzyme system is employed will be found in example 2 below. By regulating the reaction conditions for enzyme treatment, as for instance an altered flow rate of the starch solution through the column, solutions are obtained having a varying content of maltose (table II) which are suitable for various fields of application. The starch conversion product obtained in the process according to the invention can be used in the confectionery industry owing to its reduced tendency of crystallization as compared to solutions having a high glucose content, and its non-hygroscopic nature. The product can also be used in brewing beer by means of direct fermentation. Maltose is further an important carbon source in the manufacturing of special vaccines, antibiotics and enzymes. Maltitol which is a sweetening material can be manufactured by means of hydrogenation using maltose as a starting material.

EXAMPLE 1

Manufacturing of a matrix bonded two-enzyme system: β-amylase/pullulanase coupled to an acrylic polymer Dry matrix grains of "Bio-Gel CM 100" (a cross-linked copolymer of acrylamide-acrylic acid available from Bio-Rad Lab, Richmond, California, the United States of America), 100 mg, were subjected to swelling in a 0.1 M citrate-phosphate buffer, pH 4.0 (20 ml) for 2 hours under venting in an desiccator at room temperature. After excess liquid has been removed on a sintered glass filter the swollen gel is mixed with a solution of β-amylase protein (1.71 mg) in 0.1 M citrate-phosphate buffer, pH 4.0 (10 ml) in a 20 ml test tube at 4° C. The adsorption of the enzyme on the gel took place under careful shaking for 30 minutes. Then 150 mg of 1-cyclohexyl-3-(2-morpholinoethyl)-carbodiimide-metho-p-toluenesulphonate, called CMDI, available from Aldrich Chemical Co, Milwaukee, Wis., the United States of America, were added and the shaking was continued for 18 hours. The grains of enzyme-gel were then filtered away and washed on a sintered glass filter by means of distilled water (200 ml) and 0.1 M citrate-phosphate buffer, pH 4.2 (50 ml). To a solution of pullulanase protein (9.3 mg) in 0.1 M citrate-phosphate buffer, pH 4.2 (10 ml), in a 20 ml test tube, pullulane (60 mg) was added at 4° C. After 5 minutes the newly washed β-amylase-gel grains were mixed with the solution. The adsorption process was performed as described above followed by the admixture of a new portion of CMDI (50 mg). The coupling continued under careful shaking for another 18 hours at 4° C. The enzyme-gel grains were then filtered, washed and stirred for 30 minutes in distilled water (200 ml) and for 30 minutes in 0.01 M phosphate buffer, pH 7.0 (600 ml).

It appears from the above example that the coupling was performed in two consecutive steps owing to the different optimal coupling conditions of the enzymes, β-amylase being coupled in the first step due to its greater stability to high concentrations of CMDI. In the following table I the coupling yields for β-amylase protein (40%) and pullulanase protein (38%) with the remaining enzymatic activity amounting to 22% and 32%, respectively, are shown. The matrix contained 323 units of β-amylase activity and 49 units of pullulanase activity per gram of dry polymer. One unit of β-amylase activity is defined as the quantity of enzyme that liberates 1 μmol of maltose from soluble starch per minute at a pH of 4.8 and at 35° C. One unit of pullulanase activity corresponds to the quantity of enzyme producing 1 μmol of maltotriose per minute at pH 5.0 and at 30° C when pullulane is used as a starting material.

Table I

Covalent coupling of β-amylase and pullulanase to an inert acrylic copolymer

| | Bonded protein, mg/g of dry polymer | | Coupling yields based on the quantity of added enzymes, % | | β-amylase activity | | Pullulanase activity | |
|---|---|---|---|---|---|---|---|---|
| | β-amylase | pullulanase | β-amylase | pullulanase | units/mg bonded protein | residual enzyme activity % | units/mg bonded protein | residual enzyme activity % |
| "Bio-Gel CM-100" | 6.8 | 35.3 | 40 | 38 | 47.5 | 22 | 1.39 | 32 |

EXAMPLE 2

The use of a matrix bonded enzyme system for manufacturing maltose

A gelatinized substrate solution of an α-amylase hydrolyzed potato starch (dextrose equivalent 7.0) having a dry solid content of 15% in 0.01 M phosphate buffer of pH 6.0 is set at 45° C and is passed through a column comprising a bed of the matrix bonded enzyme system described in example 1. The column is temperature regulated to 45° C. The bed has a height of 30 cm and a diameter of 2.4 cm and the quantity of matrix amounted to 1.35 g of dry gel. The results of the analysis of the obtained starch hydrolysate rich in maltose will appear from table II below.

TABLE II

An analysis of conversion products of hydrolysed potato starch having a dextrose equivalent of 7.0 at various flow rates when using β-amylase pullulanase coupled to an acrylic polymer in a packed column.

| Flow rate ml/h | Glucose % by weight | Maltose % by weight | Maltotriose % by weight | Other kind of sugar % by weight |
|---|---|---|---|---|
| 13.8 | 0.3 | 70.0 | 15.8 | 13.9 |
| 34.5 | 0.3 | 65.9 | 14.2 | 19.6 |
| 69.0 | 0.2 | 60.5 | 13.4 | 25.9 |

EXAMPLE 3

A long-time stability test of the immobilized β-amylase pullulanase system was made by feeding a starch solution under operational conditions through a column containing the immobilized preparation in a packed bed. The matrix was that used in Example 1. It was necessary to operate with a continuous feed of low concentration to avoid plugging, with the equipment at hand. The decrease in degree of conversion in a period of four weeks, using constant flow rate is shown on the drawing.

What we claim is:

1. A method of enzymatic manufacturing of a starch conversion product having a high maltose content, using as a starting material a solution of a substrate comprising starch or a partial hydrolysate thereof comprising bringing the substrate solution into contact with a matrix consisting of a copolymer of acrylamide and acrylic acid to which both an α-1.6-glucosidase and an α-1,4-glucosidase having β-amylase activity have been covalently coupled by a carbodiimide.

2. The method of claim 1 wherein said α-1,6-glucosidase is pullulanase.

3. The method of claim 1 wherein said α-1,6-glucosidase is isoamylase.

4. A method according to claim 1 wherein α-1,4-glucosidase is β-amylase.

5. A method according to claim 1 wherein said substrate is a gelatinized starch hydrolysed to a dextrose equivalent of between 0.5 and 20 and wherein a starch hydrolysate containing at least 55% of maltose based on the dry content is obtained as an end product.

6. A method according to claim 1 wherein said enzymatic treatment takes place continuously.

7. A method according to claim 1 wherein the dry content of substrate amounts to between 10 and 40%.

8. A method according to claim 1 wherein the pH-value of the substrate amounts to between 4.5 and 8.

9. A method according to claim 1 wherein said enzymatic treatment takes place at a temperature of between 30° and 60° C.

10. A method according to claim 1 wherein the carbodiimide is 1-cyclohexyl-3-(2-morpholinoethyl)-carbodiimide-metho-p-toluenesulphonate.

* * * * *